(12) United States Patent
Himmelsbach et al.

(10) Patent No.: US 6,524,699 B1
(45) Date of Patent: *Feb. 25, 2003

(54) SELF-ADHESIVELY TREATED BACKING MATERIAL

(75) Inventors: Peter Himmelsbach, Buxtehude (DE); Peter Jauchen, Hamburg (DE)

(73) Assignee: Beiersdorf AG, Hamburg (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/183,114

(22) Filed: Oct. 30, 1998

(30) Foreign Application Priority Data

Dec. 12, 1997 (DE) .......................... 197 55 222

(51) Int. Cl.⁷ ............................... B32B 27/00
(52) U.S. Cl. ............... 428/343; 428/349; 428/355 AC; 428/911; 428/912; 428/914; 428/915; 428/916
(58) Field of Search ................ 428/343, 349, 428/355 BL, 911, 912, 914, 915, 916

(56) References Cited

U.S. PATENT DOCUMENTS

| 4,024,312 A | * | 5/1977 | Korpman ................... 428/343 |
| 4,049,483 A | * | 9/1977 | Loder et al. ................ 156/230 |
| 4,652,473 A | * | 3/1987 | Han ............................. 428/35 |
| 4,652,491 A | * | 3/1987 | Gorban ....................... 428/355 |
| 4,675,232 A | * | 6/1987 | Edenbaum et al. ....... 428/317.3 |
| 4,728,572 A | * | 3/1988 | Davis |
| 4,743,249 A | * | 5/1988 | Loveland ................... 424/447 |
| 5,028,485 A | * | 7/1991 | Van Hooijdonk ........... 428/355 |
| 5,051,259 A | * | 9/1991 | Olsen et al. ................ 424/443 |
| 5,389,438 A | * | 2/1995 | Miller et al. ............... 428/355 |
| 5,641,506 A | * | 6/1997 | Talke et al. ................. 424/443 |
| 5,807,637 A | * | 9/1998 | Schumann et al. ....... 428/423.1 |
| 5,820,578 A | * | 10/1998 | Johansen ..................... 602/57 |
| 5,851,664 A | * | 12/1998 | Bennett et al. ....... 428/355 BL |

FOREIGN PATENT DOCUMENTS

EP   0747027   12/1996   ........... A61F/13/02

OTHER PUBLICATIONS

"Removable Adhesive Tape", WO 92/11333, Int. Class C09J7/02, Kreckel et al. Jul. 9, 1992.*
"A Novel Discontinuous Adhesive Surface", Euprpean Patent Application 0 353 972, Int. Clas A 61F 13/02; C09J 7/00, Jul. 31, 1989.*
English–language counterpart to DE 19620107 U.S. Ser. No. 09/171,175, filed Oct. 14, 1998.

\* cited by examiner

*Primary Examiner*—Elizabeth M. Cole
*Assistant Examiner*—Arti R. Singh
(74) *Attorney, Agent, or Firm*—Norris McLaughlin & Marcus

(57) ABSTRACT

At least one-sidedly self-adhesively treated backing material which is coated partially with a self-adhesive composition and which under a tensile load of 10 N/cm has an extension of greater than 10% so that the backing material following application can be detached from the substrate by pulling in the direction of the bond plane.

18 Claims, No Drawings

SELF-ADHESIVELY TREATED BACKING MATERIAL

The invention relates to a backing material which has been self-adhesively treated on at least one side and which is partially coated.

Adhesively coated backing systems which unstick when the backing is pulled are known. They are generally based on elastic systems, which in many cases constitute laminates.

DE-A 27 28 346 describes such a laminate, consisting of an extensible film and an adhesive composition based on A-B-A block copolymers. The laminate, adhering in its entirety, is easily detached from the substrate by stretching.

The adhesive composition is always applied over the entire area. However, such whole-area application is associated with a large number of disadvantages which greatly restrict use in the medical sector, in particular. Whole-area application entails the need for large quantities of adhesive composition, which makes the production process and hence the end product as well more expensive. In addition, it is important that the backing material coated with the adhesive composition continues, following its application to the skin, to be permeable to air and water vapour, in order, for example, that perspiration can be transported away from the skin. This property is possessed only to a very limited extent, if at all, by a wholly coated backing.

DE-A 195 31 696 describes an adhesive-film laminate which is produced from an extensible backing and an acrylate adhesive composition.

WO 95/06691 discloses a redetachable adhesive tape having a foam as its backing material.

WO 92/11333 describes a system which can be removed nondestructively and possesses high tear strength. Likewise, however, partial coating is not described.

It is also known to apply self-adhesive compositions to backing materials for sheetlike structures which can be redetached without residue, and/or for medical applications, not only over the entire area but also in the form of a pattern of dots for example by means of screen printing (DE-C 42 37 252), in which case the dots of adhesive can also differ in their size and/or distribution (EP-B 353 972), or by intaglio printing, in lines which interconnect in the longitudinal and transverse directions (DE-C 43 08 649). The documents listed, however, do not describe a detachment effect (stripping effect) induced by extension of the respective backing in the orientation of the backing.

All of the systems described above have a serious disadvantage in that they have been coated over the entire area. As a result, redetachment requires a comparatively high force, thereby reaching the limit of the strength of the backing materials.

A further disadvantage of these backing materials is that in the case of whole-area coating the systems used may use their elasticity if the adhesive systems employed are of lower elasticity.

For processing, the abovementioned adhesive compositions may be present in a carrier matrix. The term carrier matrix is understood to refer to common organic or inorganic solvents or dispersion media.

Systems without a carrier matrix are referred to as 100% systems and are likewise not unknown. They are processed in the elastic or thermoplastic state. A common mode of processing is that of the melt.

Hotmelt adhesive compositions of this kind have also been described in the prior art. They are based on natural or synthetic rubbers and/or on other synthetic polymers.

Because of their high level of hardness, sticking to the skin is a problem for such 100% systems.

An advantage of the 100% systems is that they avoid an operation of removal of the carrier matrix, i.e. the auxiliary media, thereby raising the productivity of processing and at the same time reducing the expenditure on machinery and the energy costs. In addition, this reduces the occurrence of residues of the carrier matrix, which, in turn, is to the benefit of a reduction in the allergenic potential in the case of use specifically for bonding to the skin.

The object of the invention was to avoid the disadvantages known from the prior art and to provide an at least one-sidedly self-adhesive backing material which following application to the skin can be redetached by extension in a simple manner and, especially when used as a medical product, painlessly.

This object is achieved by an at least one-sidedly self-adhesively treated backing material which is partially coated with an adhesive composition and has an extension of more than 10% under a tensile load of 10 N/cm, so that following application the backing material can be detached from the substrate by pulling in the direction of the bond plane.

Under a tensile load of 10 N/cm the backing material preferably has an extension of more than 15% up to 3000%, with particular preference from 20% to 1000%.

It has been found advantageous that with the use of backing materials permeable to water vapour or air and at high application rates of more than 15 g of composition per $m^2$, the adhesively, treated products had an extremely high permeability.

Suitable backing materials are extensible sheetlike structures composed of synthetic and natural raw materials. Preference is given to backing materials which, following the application of the self-adhesive composition, can be used in such a way that they fulfill the characteristics of a functional bandage. Examples are textiles such as wovens, knits, lays, nonwovens, laminates, nets, films, foams and papers having an extensibility of at least 10% under a load of 10 N/cm.

Combinations of these materials are also suitable.

In addition, these materials can be pretreated or aftertreated. Common pretreatments are corona and hydrophobicization; customary aftertreatments are calendering, thermal conditioning, laminating, punching and lining, UV/IR irradiation or electron-beam irradiation.

For the coating it is possible as self-adhesive compositions to employ thermoplastic hotmelt adhesive compositions based on natural and synthetic rubbers and on other synthetic polymers such as acrylates, methacrylates, polyurethanes, polyolefins, polyvinyl derivatives, polyesters or silicones with corresponding additives such as tackifier resins, plasticizers, stabilizers and other auxiliaries where necessary.

Their softening point should be higher than 50° C., since the temperature of application is generally at least 90° C. and, preferably, between 120 and 150° C., or between 180 and 220° C. in the case of silicones. Postcrosslinking by means of UV or electron-beam irradiation may be appropriate, if desired.

Hotmelt adhesive compositions based on block copolymers, in particular, are notable for their diverse variation options, since the controlled reduction in the glass transition temperature of the self-adhesive composition as a result of the selection of the tackifiers, plasticizers, polymer molecule size and molecular distribution of the starting components ensures the required bonding, especially to the skin, in a manner appropriate to their function, even at critical points of the human locomotor system.

The high shear strength of the hotmelt adhesive composition is achieved through the high cohesiveness of the polymer. The good tack results from the range of tackifiers and plasticizers employed.

The hotmelt adhesive composition is based preferably on block copolymers, especially A-B or A-B-A block copolymers or mixtures thereof. The hard phase A is primarily polystyrene or its derivatives, and the soft phase B comprises ethylene, propylene, butylene, butadiene, isoprene or mixtures thereof, particular preference being given to ethylene and butylene or their mixtures.

However, polystyrene blocks may also be present in the soft phase B, in an amount of up to 20% by weight. The overall proportion of styrene, however, should always be less than 35% by weight. Preference is given to styrene contents of between 5 and 30%, since a lower styrene content makes the adhesive composition more conforming.

The controlled blending of diblock and triblock copolymers is particularly advantageous, preference being given to a proportion of diblock copolymers of less than 80% by weight.

In one advantageous embodiment the hotmelt adhesive composition has the following composition:

from 10 to 90% by weight of block copolymers, from 5 to 80% by weight of tackifiers, such as oils, waxes, resins and/or mixtures thereof, preferably mixtures of resins and oils, if desired, less than 60% by weight of plasticizers, less than 15% by weight of additives, less than 5% by weight of stabilizers.

The aliphatic or aromatic oils, waxes and resins used as tackifiers are preferably hydrocarbon oils, waxes and resins, the consistency of the oils, such as paraffinic hydrocarbon oils, or of the waxes, such as paraffinic hydrocarbon waxes, accounting for their favourable effect on bonding to the skin. Plasticizers used are medium- or long-chain fatty acids and/or their esters. These additions serve to establish the adhesion properties and the stability. If desired, further stabilizers and other auxiliaries are employed.

The adhesive composition can be filled with mineral fillers, fibres or hollow or solid microbeads.

The hotmelt self-adhesive composition has a softening point of more than 70° C., preferably from 95 to 120° C.

The hotmelt self-adhesive compositions are preferably formulated such that at a frequency of 0.1 rad/s they have a dynamic-complex glass transition temperature of less than 5° C., preferably from −3 to −30° C. and, with very particular preference, from −9 to −25° C.

Medical products in particular are subject to stringent requirements in terms of their adhesion properties. For ideal application, the hotmelt adhesive composition should possess a high tack. There should be functionally appropriate bond strength to the skin and the reverse of the backing. So that there is no slipping, moreover, the hotmelt adhesive composition is required to have a high shear strength.

The controlled reduction in the glass transition temperature of the self-adhesive composition, which is essential to the invention and a consequence of the selection of the tackifiers, of the plasticizers and of the polymer molecule size and the molecular distribution of the starting components, achieves the required bonding, in a manner appropriate to its function, to the skin and to the reverse of the backing. The high shear strength of the self-adhesive composition employed here is achieved through the high cohesiveness of the block copolymer. The good tack arises from the range of tackifiers and plasticizers employed.

Product properties such as tack, glass transition temperature and shear stability can be quantified readily by means of a dynamomechanical frequency measurement. In this case, use is made of a rheometer controlled by shearing stress.

The results of this measurement method give information on the physical properties of a substance by taking into account the viscoelastic component. In this instance, at a preset temperature, the hotmelt self-adhesive composition is set in oscillation between two plane-parallel plates with variable frequencies and low deformation (linear viscoelastic region). Via a pickup control unit, with computer assistance, the quotient (Q=tan δ) between the loss modulus (G", viscous component) and the storage modulus (G', elastic component) is determined.

$$Q = \tan \delta = G''/G'$$

A high frequency is chosen for the subjective sensing of the tack and a low frequency for the shear strength.

A high numerical value denotes better tack and poorer shear stability.

The glass transition temperature is that temperature at which amorphous or partially crystallized polymers undergo transition from the liquid or rubber-elastic state into the hard-elastic or glassy state, or vice versa (Römpp Chemie-Lexikon, 9th Ed. Vol. 2, page 1587, Georg Thieme Verlag Stuttgart—New York, 1990). It corresponds to the maximum of the temperature function at a predetermined frequency.

For medical applications in particular, a relatively low glass transition point is required.

| Designation | $T_g$ low frequency | Conformity Low frequency/RT | Tack high frequency/RT |
| --- | --- | --- | --- |
| Hotmelt adhesive composition A | −12 ± 2° C. | Tan δ = 0.08 ± 0.03 | tan δ = 0.84 ± 0.03 |
| Hotmelt adhesive composition B | −9 ± 2° C. | Tan δ = 0.32 ± 0.03 | tan δ = 1.70 ± 0.03 |

In accordance with the invention, preference is given to hotmelt adhesive components for which the ratio of the viscous component to the elastic component at a frequency of 100 rad/s and 25° C. is greater than 0.7, preferably from 1.0 to 5.0, or to hotmelt self-adhesive compositions for which the ratio of the viscous component to the elastic component at a frequency of 0.1 rad/s and 25° C. is less than 0.4, preferably between 0.35 and 0.02 and, with very particular preference, between 0.3 and 0.1.

It is also advantageous, especially for use in connection with medical products, if the hotmelt adhesive composition is applied partially to the backing material, by means for example of halftone printing, thermal screen printing, thermal flexographic printing or intaglio printing, because backing materials which have been adhesively treated in a continuous applied line may easily induce mechanical skin irritations when applied.

Partial application makes it possible to dissipate the transepidermal water loss through controlled channels and improves the removal of perspiration from the skin in vapour form, especially when the backing materials used are permeable to air and water vapour. This avoids skin irritations induced by buildup of body fluids. The dissipation channels that have been set up enable fluids to be conducted away, even when a multi-ply bandage is used.

In addition, in the case of backing materials with a high weight per unit area and low extension, as are common, for example, for short-term dressing, the partial coating actually enables redetachment by extension in a manner which, despite the high bond strength of these adhesive dressing systems, is extremely painless.

Preference is given to application in the form of polygeometric domes and, in particular, of those domes where the ratio of diameter to height is less than 5:1. Printed application of other forms and patterns on the backing material is also possible—for example, a printed image in the form of alphanumeric character combinations or patterns such as matrices, stripes, assemblies of domes, and zigzag lines.

In addition, for example, the composition can be applied by spraying, so producing a more or less irregular applied pattern.

The self-adhesive composition can be distributed uniformly over the backing material; alternatively, it can be applied with a thickness or density which varies over the area, as appropriate to the function of the product.

The principle of thermal screen printing lies in the use of a rotating, heated, seamless, drum-shaped, perforated, cylindrical screen which is fed via a nozzle with the preferred hotmelt self-adhesive composition. A specially shaped nozzle lip (circular-gap or square-section coating bar) presses the hotmelt adhesive composition, which is fed in via a channel, through the perforation of the screen wall and onto the backing web that is conveyed past it. This backing web is guided by means of a counterpressure roller against the external jacket of the heated screen drum at a rate which corresponds to the peripheral speed of the rotating screen drum.

In this process, the formation of the small domes of adhesive takes place according to the following mechanism:

The pressure of the nozzle coating bar conveys the hotmelt adhesive composition through the screen perforation onto the backing material. The size of the domes formed is defined by the diameter of the screen perforation. The screen is lifted from the backing in accordance with the rate of transportation of the backing web (rotary speed of the screen drum). As a consequence of the high adhesion of the self-adhesive composition and of the internal cohesion of the hotmelt, the limited supply of hotmelt adhesive composition in the perforations is drawn in sharp definition from the base of the domes, which is already adhering to the backing, and is conveyed onto the backing by the pressure of the coating bar.

Following the end of this transportation, the more or less highly curved surface of the dome forms over the predefined base area in dependence on the rheology of the hotmelt adhesive composition. The height-to-base ratio of the dome depends on the ratio of perforation diameter to the wall thickness of the screen drum and on the physical properties (flow, surface tension and contact angle on the backing material) of the self-adhesive composition.

For the screen in thermal screen printing the web-to-hole ratio can be less than 3:1, preferably less than or equal to 1:1 and, in particular, equal to 1:3.

The above-described mechanism of formation of the domes requires, preferentially, backing materials that are absorbent or at least wettable by hotmelt adhesive composition. Non-wetting backing surfaces must be pretreated by chemical or physical methods. This can be done by means of additional measures such as corona discharge, for example, or by coating with substances which improve wetting.

Using the printing technique indicated it is possible to lay down the size and shape of the domes in a defined manner. The bond strength values which are relevant for use, i.e. those which determine the quality of the products formed, are within very narrow tolerances provided that coating is carried out correctly. The base diameter of the domes can be chosen to be from 10 to 5000 $\mu$m, the height of the domes from 20 to about 2000 $\mu$m and, preferably, from 50 to 1000 $\mu$m, the low-diameter range being intended for smooth backings and the range of greater diameter and greater dome height being intended for rough or highly porous backing materials.

The positioning of the domes on the backing is laid down in a defined manner by the geometry of the applicator unit, for example the gravure or screen geometry, which can be varied within wide limits. With the aid of the parameters indicated it is possible by way of adjustable variables to establish with very great precision the desired profile of properties of the coating, harmonized with the various backing materials and applications.

The backing material is preferably coated at a rate of more than 2 m/min, preferably from 20 to 220 m/min, the chosen coating temperature being greater than the softening point.

The hotmelt adhesive composition can be applied to the backing material in a weight per unit area of more than 15 g/m$^2$, preferably between 20 and 300 g/m$^2$ and, with very particular preference, between 90 and 160 g/m$^2$.

The percentage area which is coated with the hotmelt adhesive composition should be at least 20% and can extend up to approximately 95%, for specific products preferably from 40 to 60% and from 70 to 95%. This can be achieved if desired by means of multiple application, with the possible use if desired of hotmelt adhesive composition s having different properties.

It has also been found advantageous to load the adhesive with gas so as to improve the performance properties. In this way it is possible, for example, for better conformity and an increase in the initial bond strength to occur. It is preferred to load the hotmelt self-adhesive composition with a gas content of more than 5% by volume, preferably from 20 to 85% by volume.

The combination of the hotmelt adhesive composition and the partial coating firstly ensures secure bonding of the medical product to the skin and secondly rules out allergic or mechanical skin irritations—at least those which are visually discernible—in the case even of an application which extends over several days.

The epilation of corresponding body regions and the transfer of composition to the skin are negligible owing to the high cohesiveness of the adhesive, since the adhesive is not anchored to skin and hair—rather, the anchorage of the self-adhesive composition to the backing material, at up to 12 N/cm (sample width), is good for medical applications.

Because of the intended breakage points which have been formed in the coating, layers of skin are no longer displaced with one another or against one another in the course of detachment. The non-displacement of the layers of skin and the relatively low level of epilation lead to an unprecedented degree of painlessness in such strongly adhering systems. The applied backing material shows good proprioreceptive effects.

Depending on the backing material and its temperature sensitivity, the hotmelt adhesive composition can be applied directly or can be applied first to an auxiliary support and then transferred to the ultimate backing. Subsequent calandering of the coated product and/or pretreatment of the backing, such as corona irradiation, may be advantageous for better anchorage of the adhesive film.

The backing material coated with the adhesive coating composition can have an air permeability of greater than 1 cm$^3$/(cm$^2$*s), preferably greater than 15 cm$^3$/(cm$^2$*s) and, with very particular preference, greater than 70 cm³/(cm²*s) and a water vapour permeability of greater than 500 g/(M²*24h), preferably greater than 1000 g/(m²*24h), and, with very particular preference, greater than 2000 g/(m²*24h).

Following the coating operation, finally, the backing material can be lined with an anti-adhesive backing material, such as siliconized paper, or provided with a wound pad or padding.

It is particularly advantageous that the self-adhesively treated backing material can be sterilized, preferably by means of γ (gamma) radiation. Consequently, particular suitability for subsequent sterilization is possessed by block copolymer-based hotmelt adhesive compositions which contain no double bonds. This applies in particular to styrene-butylene-ethylene-styrene block copolymers or styrene-butylene-styrene block copolymers. In this case the adhesive properties are not subject to any changes significant for the application.

Finally, the self-adhesive composition may comprise an active substance. In the case of doped self-adhesive compositions, particular preference is given to those which release substances.

The backing material of the invention has a bond strength to the reverse of the backing of at least 0.5 N/cm, in particular between 1 and 5 N/cm. Higher bond strengths may be achieved on other substrates.

The outstanding properties of the self-adhesively treated backing material of the invention suggest its use for medical products, especially plasters, medical fixings, wound coverings, orthopaedic or phlebological bandages, and dressings.

In the text below, the self-adhesively treated backing material of the invention will be depicted by means of examples, without wishing thereby unnecessarily to restrict the invention.

EXAMPLE 1

In accordance with the invention, an elastic self-adhesive bandage was produced which owing to its properties, described below, can be used as a functional dressing, the functional dressing technique being guided by the anatomy and biomechanics.

The bandage used for this type of dressing consisted of an elastic woven cotton fabric with a breaking strength of more than 80 N/cm and a breaking extension of more than 100%. The extensibility at 10 N/cm of the uncoated backing material was 75% and was not substantially lowered by the coating.

The self-adhesive composition was applied to the backing by thermal screen printing, and was a hotmelt adhesive composition having the following composition:
 an A-B/A-B-A block copolymer consisting of hard and soft segments, with a ratio of A-B-A to A-B of 2:1 and a styrene content in the polymer of 13 mol %; its proportion in the self-adhesive composition was 40% by weight (Kraton G)
 a paraffinic hydrocarbon wax whose proportion in the adhesive composition is 52% by weight
 hydrocarbon resins with a proportion of 7.5% by weight (Super Resin HC 140)
 an anti-ageing agent with a proportion of less than 0.5% by weight (Irganox).

The components employed were homogenized in a thermal mixer at 175° C.

The softening point of this self-adhesive composition was 95° C. (DIN 52011), and the adhesive composition had a viscosity of 2100 mPas at 150° C. (DIN 53018, Brookfield DV II, sp. 21). The glass transition according to the method indicated above was −8° C.

Direct coating took place at 50 m/min and at a temperature of 130° C. The backing material was coated in dot form at 120 g/m² using a 14 mesh screen with a thickness of 300 μm.

The bandage produced by this method exhibited good detachability by extension in the orientation of the skin surface and had good permeability to air and water vapour. Because of the high shear stability of the hotmelt pressure-sensitive adhesive, sufficient stabilization and a good proprioreceptive effect were found. No skin irritations, and a negligible degree of epilation, were observed after the bandage had been removed.

A comparative investigation on steel showed that the shear force required to detach the bandage has approximately only a third of the shear force exhibited by a bandage material coated over the whole area at the same rate of application of adhesive composition.

EXAMPLE 2

A filter material redetachable by extension was produced, this material being based on an elastic nonwoven. The filtering effect of this filter material was obtained through the partial coating.

The filter material consisted of a commercially customary filter nonwoven having thermoplastic properties. The nonwoven had a breaking extension of 250% and an extension under 10 N/cm load of 150%.

The block copolymer was a styrene-ethylene-butylene-styrene block copolymer to which paraffinic hydrocarbon wax had been added. The proportion was one part of polymer to one part of paraffinic hydrocarbon. 10% polystyrene resin (Amoco 18240) was added to this mixture. The adhesive contained one per cent of Irganox, an anti-ageing agent (n-octadecyl β-(3,5-di-t-butyl-4-hydroxyphenyl) propionate), and further hydrocarbon resins and fatty acid esters, which were present only in small amounts in the overall adhesive. The softening point of this self-adhesive composition was 100° C. (DIN 52011) and the glass transition temperature, determined by the method set out above, was −6° C.

Using a 40 mesh screen with an open area of 20% it was possible to achieve an adhesive composition application rate of 20 g/m².

The filter material produced in this way was of high air permeability: more than 85 cm³/(cm²*s).

The elastic, adhesive filter device was found to be advantageous owing to its rapid removability, especially when used at frequently changing sites. The whole-side partial coating likewise resulted in rapid and easy assembly of these filter materials. The shear force was 6 N/cm.

What is claimed is:

1. An adhesive article comprising a backing material coated on at least one surface thereof with a pressure sensitive adhesive composition, said pressure sensitive adhesive composition being coated on said at least one surface in a plurality of discrete and discontinuous areas of pressure sensitive adhesive composition such that the pressure sensitive adhesive composition only partially coats said surface, and wherein the adhesive article under a tensile load of 10 N/cm has an extension of greater than 10% and, when bonded to a substrate, can be removed from the substrate by pulling on the adhesive article in the direction of the plane of the bond formed by the bonding of said adhesive article in the direction of the plane of the bond formed by the bonding of said adhesive article to said substrate.

2. The adhesive article according to claim 1, which under a tensile load of 10 N/cm has an extension of greater than 15% up to 3000%.

3. The adhesive article according to claim 1, wherein the self-adhesive composition is a hotmelt adhesive composition having a dynamic-complex glass transition temperature with a frequency of 0.1 rad/s of less than 5° C.

4. The adhesive article according to claim 1, wherein the hotmelt adhesive composition is built up on the basis of block copolymers.

5. The adhesive article according to claim 4, wherein the block copolymers are A-B or A-B-A block copolymers or mixtures thereof, with phase A being principally polystyrene or its derivatives and phase B being ethylene, propylene, butylene, butadiene, isoprene or mixtures thereof.

6. The adhesive article according to claim 1, wherein the hotmelt adhesive composition consists of from 10 to 90% by weight of block copolymers, from 5 to 80% by weight of tackifiers, if desired, less than 60% by weight of plasticizers, less than 15% by weight of additives, less than 5% by weight of stabilizers.

7. The adhesive article according to claim 6, wherein the tackifiers are selected from the group consisting of oils, waxes, resins and mixtures thereof.

8. The adhesive article according to claim 7, wherein the tackifiers are selected from the group consisting of mixtures of resins and oils.

9. The adhesive article according to claim 1, wherein the hotmelt adhesive composition is applied by halftone printing, thermal screening printing or intaglio printing.

10. The adhesive article according to claim 1, wherein the hotmelt adhesive composition is applied in the form of polygeometric domes to the backing material.

11. The adhesive article according to claim 1, wherein the hotmelt adhesive composition has been coated onto the backing material in a weight per unit area of more than 15 g/m$^2$.

12. The adhesive article according to claim 1, wherein the coated backing material has an air permeability of greater than 1 cm$^3$/cm$^2$*s).

13. The adhesive article according to claim 1, wherein the backing material has bond strength to the reverse of the backing of at least 0.5 N/cm.

14. The adhesive article according to claim 1, wherein the hotmelt adhesive composition has a gas content of more than 5% by volume.

15. Orthopaedic or phlebological bandages and dressings comprising the adhesive article of claim 1.

16. The orthopaedic or phlebological bandages and dressings of claim 15, wherein the partially coated backing material is lined after application or provided with a wound pad or padding.

17. The orthopaedic or phlebological bandages and dressings of claim 15, wherein the partially coated backing material is sterilizable.

18. The orthopaedic or phlebological bandages and dressings of claim 15, wherein the pressure sensitive adhesive composition includes an active substance.

* * * * *